US00PP17409P2

(12) United States Plant Patent
Kolster

(10) Patent No.: US PP17,409 P2
(45) Date of Patent: Feb. 13, 2007

(54) *KOELREUTERIA PLANT* NAMED 'CORAL SUN'

(50) Latin Name: *Koelreuteria paniculata*
Varietal Denomination: CORAL SUN

(76) Inventor: Henny Kolster, Laag Boskoop 100, Boskoop (NL), 2771 GZ ( * ) Notice: Subject to any disclaimer, the term of this patent is extended or adjusted under 35 U.S.C. 154(b) by 0 days.

(21) Appl. No.: 11/208,305

(22) Filed: Aug. 18, 2005

(30) Foreign Application Priority Data

Sep. 14, 2004 (QZ) ..... PBR 2004/1713

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

UPOV ROM GTITM Computer Database, GTI Jouve Retrieval Software 2005/05 Citation for 'Coral Sun'.*
http://planthaven.com/koelcora.htm.*

* cited by examiner

*Primary Examiner*—Wendy Haas

(57) ABSTRACT

A new cultivar of *Koelreuteria* named 'CORAL SUN' that is characterized by emerging and persistent orange red spring foliage, mid-green summer foliage, bright red petioles at all times, and the typical golden yellow fall foliage for the species. In combination these traits set 'CORAL SUN' apart from all other existing varieties of *Koelreuteria* known to the inventor.

3 Drawing Sheets

Genus: *Koelreuteria.* Species: *paniculata.*
Denomination: CORAL SUN.

BACKGROUND OF THE INVENTION

The present invention relates to a new and distinct cultivar of *Koelreuteria,* known commonly as Golden Rain Tree, which is grown as an ornamental plant for use in the landscape. The new cultivar is known botanically as *Koelreuteria paniculata* and will be referred to hereinafter by the cultivar name 'CORAL SUN'.

*Koelreuteria paniculata* is widely grown and used as a small to medium sized tree in the landscape. There are no cultivars of *Koelreuteria paniculata* known to the inventor. Plants of *Koelreuteria paniculata* in commerce are considered to be plants of the species itself. Plants of *Koelreuteria paniculata* may be raised from seed, and the resulting seedlings are generally sufficiently uniform for growing on into finished plants. Alternatively, seedlings of sufficient vigor may be grafted onto rootstocks which are themselves plants of *Koelreuteria paniculata.*

In 1993, the inventor discovered 'CORAL SUN' as a single whole plant in a bed of seedlings of *Koelreuteria paniculata* which had been raised by the inventor at the inventor's nursery in Boskoop, The Netherlands. Typically, the emerging leaves on young seedlings of *Koelreuteria paniculata* are orange-red in color, which soon changes to mid green as the leaves expand and mature. The inventor observed that the emerging foliage of the single seedling 'CORAL SUN' remained orange-red in color even as the plants grew through the spring. In addition, all the leaves of the single seedling 'CORAL SUN' exhibited striking bright red petioles. As the single seedling 'CORAL SUN' grew on into summer, the foliage turned to light green (lighter than the typical mid-green of the summer growth of the species).

In addition, the red coloration of the petioles persisted and became yet more striking against the green summer foliage.

The inventor isolated and observed the single seedling 'CORAL SUN' from 1993 until 1996. In 1996, the inventor took portions of budwood from the single three year old seedling 'CORAL SUN' and grafted same onto rootstocks of *Koelreuteria paniculata.* The inventor observed all the resulting grafted progeny for three years and found that the characteristics of orange-red new spring growth and bright red petioles were stable and persistent. The inventor has determined that 'CORAL SUN' reproduces true to type in successive generations of asexual propagation.

'CORAL SUN' is most closely resembled by its species which is also the parentage. In comparison, 'CORAL SUN' and the species *Koelreuteria paniculata* appear as follows:

The spring foliage growth of the species *Koelreuteria paniculata* emerges with an orange-red coloration and soon turns to mid green, whereas the foliage of 'CORAL SUN' both emerges and persists orange-red into summer and also carries bright red petioles.

The summer foliage growth of the species *Koelreuteria paniculata* is mid-green in coloration, whereas the summer foliage of 'CORAL SUN' is light green in coloration.

A prominent and valued characteristic of *Koelreuteria paniculata* is the golden yellow color of the fall foliage. In this respect, 'CORAL SUN' is indistinct from plants of the species *Koelreuteria paniculata.*

An application for a grant of European Community Plant Breeders Rights for 'CORAL SUN' was filed by the inventors on Sep. 14, 2004, Application Number 2004/1713.

SUMMARY OF THE INVENTION

The following represent the distinguishing characteristics of the new *Koelreuteria paniculata* cultivar 'CORAL SUN'.

In combination these traits set 'CORAL SUN' apart from all other existing varieties of *Koelreuteria* known to the inventor. 'CORAL SUN' has not been tested under all possible conditions and phenotypic differences may be observed with variations in environmental, climatic, and cultural conditions, however, without any variance in genotype.

1. The emerging spring foliage of 'CORAL SUN' is orange-red in color.
2. The orange-red coloration of the spring foliage of 'CORAL SUN' persists into summer.
3. The summer foliage color of 'CORAL SUN' is light green.
4. The color of the petioles of 'CORAL SUN' are bright red at all stages when leaves are present on the plant.
5. 'CORAL SUN' exhibits the characteristic golden yellow fall foliage of the species *Koelreuteria paniculata.*

BRIEF DESCRIPTION OF THE DRAWINGS

The accompanying color drawings illustrate the overall appearance of the new *Koelreuteria* cultivar 'CORAL SUN' showing the colors as true as it is reasonably possible to obtain in colored reproductions of this type. Colors in the drawings may differ from the color values cited in the detailed botanical description, which accurately describe the actual colors of the new variety 'CORAL SUN'.

All of the drawings depict plants of 'CORAL SUN' which are approximately five years old and which are growing in the open ground in Boskoop, The Netherlands.

The drawing labeled

The drawing labeled

The drawing labeled

The drawing labeled

The drawing labeled

Figure 1:
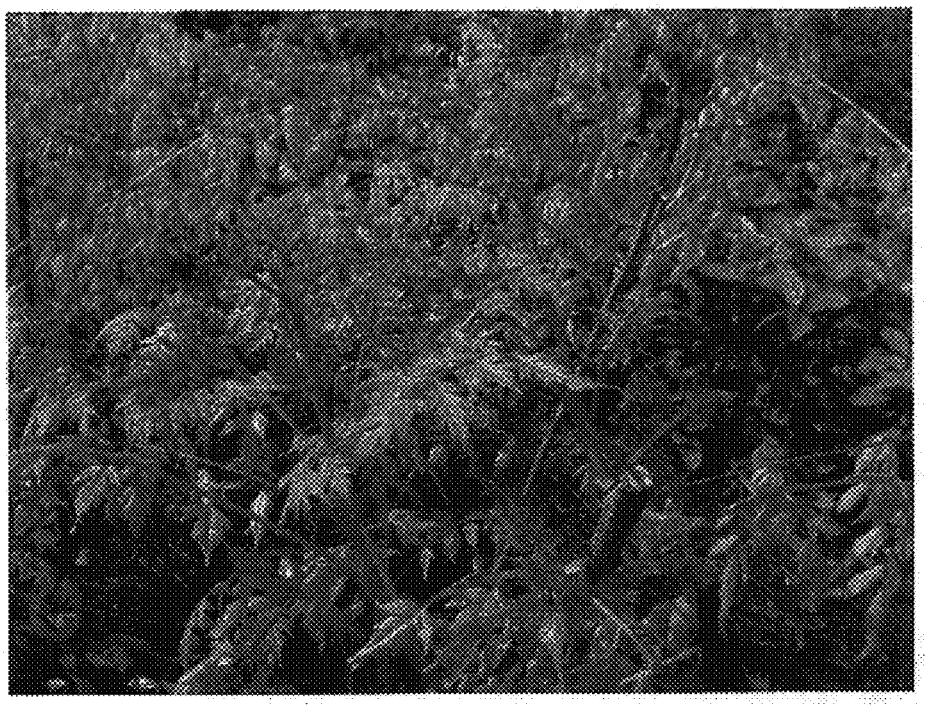
FIG. 1 shows the newly emerging spring growth on three-year old plants of 'CORAL SUN' which had been pruned in the previous winter.
Figure 2:
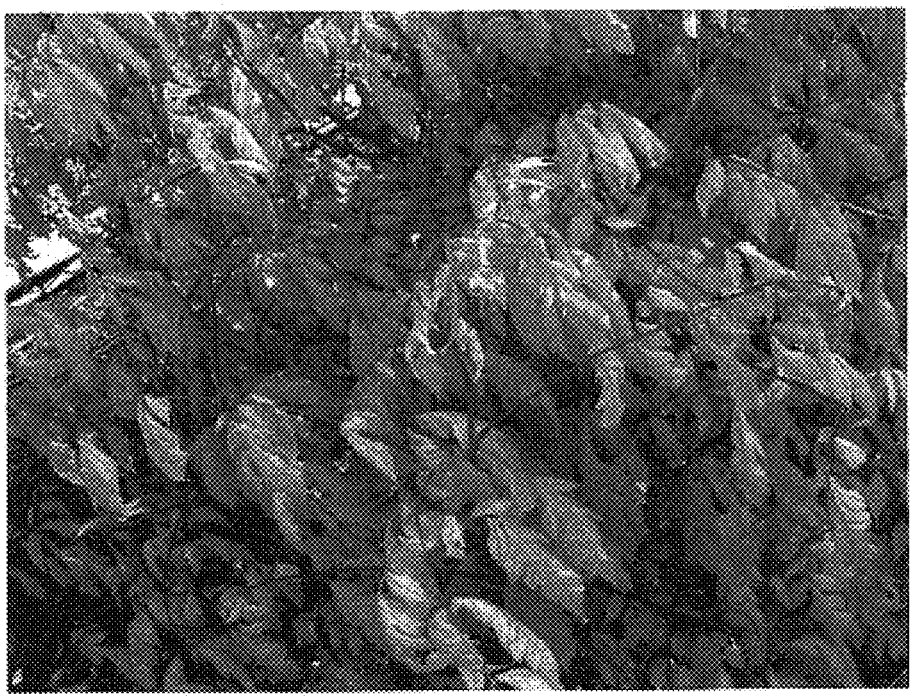
FIG. 2 is a close-up view of the foliage of 'CORAL SUN' in late spring or early summer showing the bright red petioles and the light green coloration of the foliage.
Figure 3:
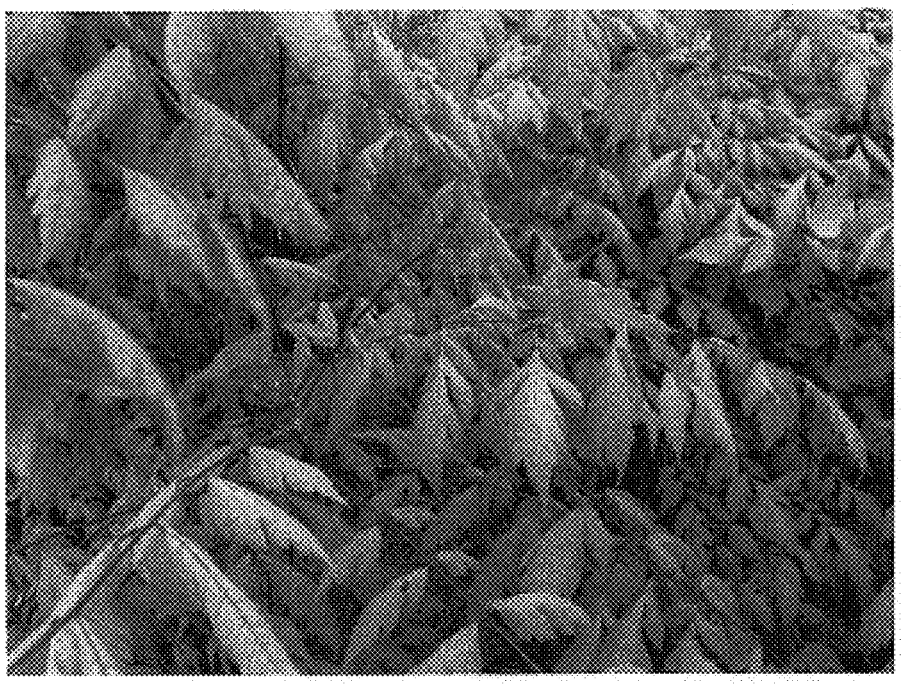
FIG. 3 is a close-up view of the foliage of 'CORAL SUN' in mid summer. This drawing depicts the predominantly light green and the bright red petioles.
Figure 4:
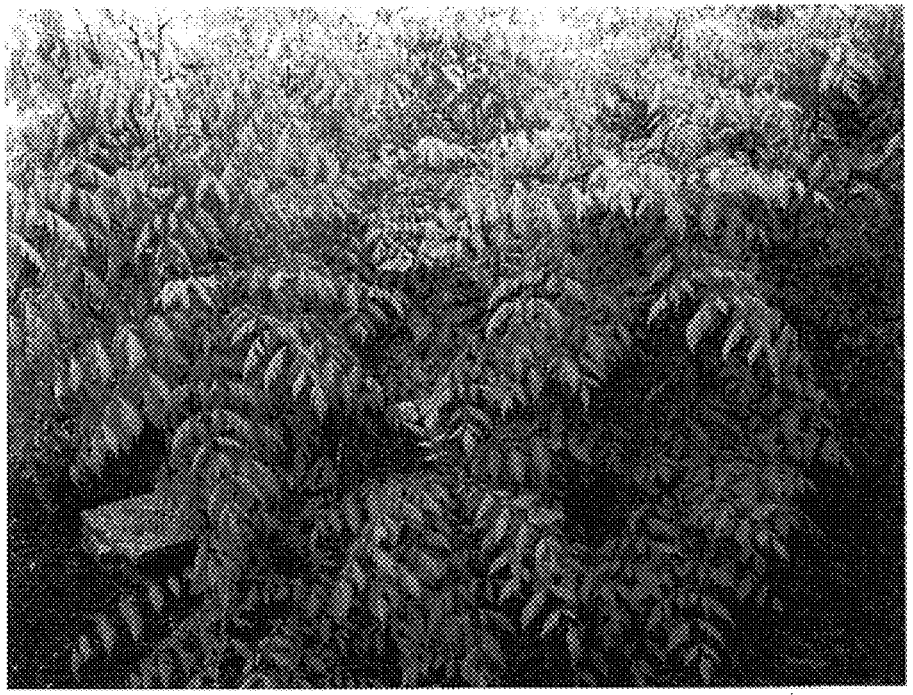
FIG. 4 illustrates a group of whole plants of 'CORAL SUN' in mid summer.
Figure 5:
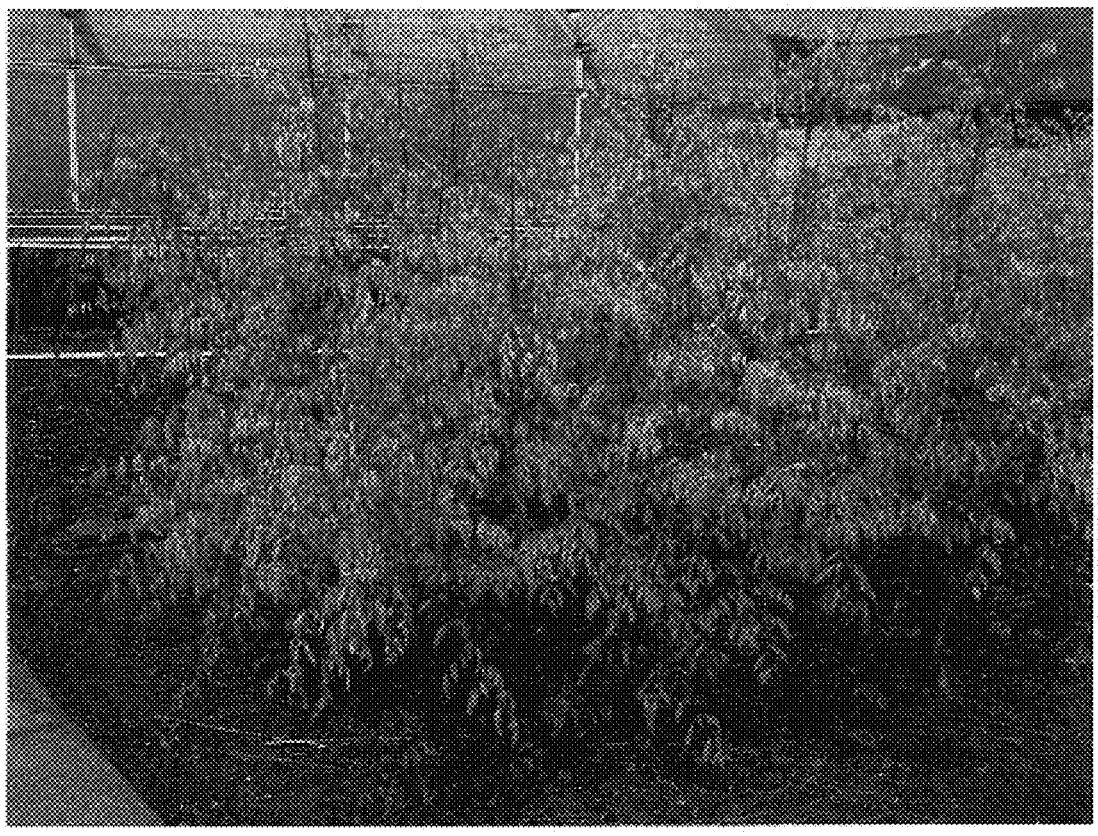
FIG. 5 illustrates a group of whole plants of 'CORAL SUN' in the fall, and showing the characteristic golden fall color of 'CORAL SUN' and of the species *Koelreuteria paniculata.*

The drawings have been made from photographs taken by conventional techniques and although foliage colors may appear different from actual colors due to light reflectance, they are as accurate as possible by conventional photography.

BOTANICAL DESCRIPTION OF THE PLANT

The following is a detailed description of the *Koelreuteria paniculata* cultivar named 'CORAL SUN'. Data was collected in Boskoop, The Netherlands from plants which are approximately five years old and which are growing, and have been grown, in the open ground without any winter protection.

Color determinations are in accordance with The Royal Horticultural Society Colour Chart, except where general color terms of ordinary dictionary significance are used. 'CORAL SUN' has not been tested under all possible conditions and phenotypic differences may be observed with variations in environmental, climatic, and cultural conditions, however, without any variance in genotype.

Botanical classification: *Koelreuteria paniculata* 'CORAL SUN'.
Genus: *Koelreuteria.*
Species: *paniculata.*
Denomination: 'CORAL SUN'.
Commercial classification: Landscape tree.
Common name: Golden Rain Tree.
Uses: Individual and mass plantings in the landscape.
Growing regime: Either field produced in the open ground and sold with a wrapped root ball, or grown in a container.
Suggested container size: 4 inch to 1 gallon container for a one or two year old plant; 3 gallon container or larger for 3 year old plants or older.
Cultural requirements: Adaptable to a wide range of soil types; prefers full sun; prune during winter.
Parentage: 'CORAL SUN' was discovered as a single seedling amongst seedlings of the species *Koelreuteria paniculata.*
Plant description:
- *Blooming season.*—No blooming has been observed to date.
- *Plant habit and form.*—Dense tree, rounded canopy, branches spreading and ascending.
- *Vigor.*—Moderately vigorous; plant growth extends by approximately 2 ft per year.
- *Plant height* (*at maturity*).—Approximately 2 meters at ten years from initial graft.
- *Plant width* (*at maturity*).—Approximately 1.1 meters at ten years from initial graft.
- *Hardiness.*—Hardy to USDA Zone 5.
- *Propagation.*—Traditionally by grafting; possible by cuttings using ripe current-season wood.
- *Root system.*—Fibrous.
- *Propagation* (*graft*) *time.*—Approximately 3 months are needed to produce a well-taken graft.
- *Propagation* (*cuttings*) *time.*—Approximately 7 months are needed to produce a well-established plant suitable for transplanting into the open ground or into a container.
- *Seasonal interest.*—Orange-red foliage in the spring; golden yellow fall color.
- *Disease and pests.*—None of note.

Branching: Moderately free branching.
- *Basal branches.*—None.
- *Lateral branches.*—Approximately 6.
- *Length of lateral branches.*—Averages 27 cm.
- *Diameter of lateral branches.*—Averages 7.5 cm.
- *Internode length.*—Average 2.9 cm.

Stem:
- *Surface.*—Young stems smooth. Older stems rough, dull, numerous lenticels.
- *Shape.*—Cylindrical.
- *Color.*—Young stems: 46A and 46B both present. Older stems: Ranges between 172C and 199B or 199C.
- *Lenticels.*—Numerous, average 20 per square cm. Young stems: length 0.5 mm; diameter 0.2 mm. Color, white: 155C. Older stems: length 0.8 mm; diameter 0.8 mm. Color, gray-brown: 199C and 199D.

Foliage:
- *Type.*—Deciduous.
- *Leaf arrangement.*—Alternate.

*Leaf division.*—Pinnate and bipinnate.
*Leaf shape.*—Ovate to oblong, slightly convexed.
*Leaf base.*—Acuminate.
*Leaf apex.*—Acute.
*Leaf venation.*—Pinnate.
*Vein color* (*adaxial surface*).—Between 181A and 181B.
*Vein color* (*abaxial surface*).—Between 181C and 181D.
*Rachis color.*—44A.
*Leaf surface* (*adaxial and abaxial*).—Densely pubescent, especially abaxial surface.
*Hairs.*—Average length approximately 1 mm, greenish-white but too small to match with Colour Chart.
*Leaf attachment.*—Petiolate.
*Petiole dimensions.*—5.6 cm in length and 3 mm. in diameter.
*Petiole color.*—44A.
*Petiole surface.*—Smooth.
*Leaf margin.*—Coarsely crenate; upper leaflets usually bi-lobed.
*Leaf length.*—45 cm.
*Leaf width.*—25 cm.
*Spring leaf colors* (*adaxial and abaxial surfaces*).—180A aging to colors between 173A and 173C.
*Summer leaf colors* (*adaxial surface*).—141C.
*Summer leaf colors* (*abaxial surface*).—Between and including 141B and 141C.
*Fall leaf color* (*both surfaces*).—Changing from 141C through 153A to N25D.
*Foliar fragrance.*—None observed.

Flowers, reproductive organs: No flowering has been observed on any plants of any age.

It is claimed:

1. A new and distinct variety of *Koelreuteria* plant named 'CORAL SUN' as described and illustrated.

* * * * *